United States Patent
Hewitson

(10) Patent No.: US 9,839,790 B2
(45) Date of Patent: Dec. 12, 2017

(54) LASER THERAPY DEVICE

(71) Applicant: Avant Wellness Systems, San Clemente, CA (US)

(72) Inventor: Andrew Hewitson, Dana Point, CA (US)

(73) Assignee: Avant Wellness Systems, Inc., Agoura Hills, CA (US)

( * ) Notice: Subject to any disclaimer, the term of this patent is extended or adjusted under 35 U.S.C. 154(b) by 0 days.

(21) Appl. No.: 14/618,008

(22) Filed: Feb. 10, 2015

(65) Prior Publication Data

US 2015/0224332 A1 Aug. 13, 2015

Related U.S. Application Data

(60) Provisional application No. 61/938,294, filed on Feb. 11, 2014, provisional application No. 61/974,531, filed on Apr. 3, 2014.

(51) Int. Cl.
*A61N 5/06* (2006.01)
*A61N 5/067* (2006.01)

(52) U.S. Cl.
CPC .......... *A61N 5/06* (2013.01); *A61N 2005/067* (2013.01); *A61N 2005/0627* (2013.01); *A61N 2005/0644* (2013.01); *A61N 2005/0651* (2013.01)

(58) Field of Classification Search
None
See application file for complete search history.

(56) References Cited

U.S. PATENT DOCUMENTS

| | | | | |
|---|---|---|---|---|
| 7,118,563 B2 * | 10/2006 | Weckwerth | .......... | A61B 18/203 606/13 |
| 8,672,987 B2 * | 3/2014 | Hottinger | ............. | A61B 18/203 606/13 |
| 8,790,382 B2 | 7/2014 | Gerlitz | | |
| 8,961,578 B2 * | 2/2015 | Liu | ....... | A61B 18/203 606/9 |
| 9,033,497 B2 * | 5/2015 | Caldeira | ............ | G02B 27/0025 351/200 |
| 2007/0239143 A1 * | 10/2007 | Altshuler | ........... | A46B 15/0036 606/9 |
| 2008/0077198 A1 * | 3/2008 | Webb | ................... | A61N 5/0618 607/88 |
| 2008/0091179 A1 * | 4/2008 | Durkin | ................ | A61B 18/203 606/9 |

(Continued)

*Primary Examiner* — Brian T Gedeon
(74) *Attorney, Agent, or Firm* — Kevin Keener; Keener and Associates P.C.

(57) ABSTRACT

A Laser therapy device that uses temperature sensing to provide clinical feedback and optical elements to produce a projection pattern for a given therapeutic application. Integrated thermal imaging provides the operator with visual representation of the tissue being treated. The optical elements are contained in a replaceable lens assembly that also contains an electronic identification chip to allow the device to automatically reconfigure behavior according to the type of lens. The device includes a wireless data transceiver that can be used for remote configuration and control. The device has the ability to modulate the output power over a wide range using a combination of pulse width modulation (PWM) and analog control techniques. The device provides on-demand audio-visual training.

11 Claims, 8 Drawing Sheets

(56) References Cited

U.S. PATENT DOCUMENTS

| | | | |
|---|---|---|---|
| 2008/0125835 A1* | 5/2008 | Laurent | A61N 5/0617 607/89 |
| 2009/0131922 A1* | 5/2009 | Dewey | A61B 18/203 606/9 |
| 2009/0240310 A1* | 9/2009 | Kennedy | A61N 5/0616 607/89 |
| 2009/0254154 A1* | 10/2009 | De Taboada | A61N 5/0613 607/88 |

* cited by examiner

LASER THERAPY DEVICE

PRIORITY

This application claims the benefit of U.S. Provisional Application No. 61/938,294, filed Feb. 11, 2014, and U.S. Provisional Application No. 61/974,531, filed Apr. 3, 2014, which are fully incorporated by reference.

FIELD OF THE INVENTION

The invention relates generally to laser therapy devices and more particularly to a handheld, cordless laser therapy device using diffractive optical elements for beam shaping, a target temperature sensing component for measuring and regulating the energy output level and target proximity sensing for safety. The present invention relates to an improved laser therapy device with specialized optical elements, temperature sensing, novel output power control, automatic hood identification, novel thermal management, optional wireless configuration and control, and on-demand audio-visual training.

BACKGROUND OF THE INVENTION

Laser therapy is used in many different treatment scenarios, from Acupuncture through to surgery recovery. The therapeutic value of laser light was discovered by accident. Surgeons noticed that surgeries that were performed using laser scalpels healed faster and better than when using traditional metal scalpels. Surgical laser devices required only a simple defocusing of the beam to be used effectively for therapy and thus are an ideal vehicle for experimentation with the therapeutic value of laser light. Due to this simple repurposing of existing technology, modern therapy lasers remain almost identical to their surgical predecessors.

While various treatment modalities uses the same basic laser technology to produce laser light, each has a different requirement for how the light is emitted (leaves the treatment device). Some modalities require tight focus of the beam down to a point (for acupuncture), others require a larger diffused beam (pain management) and certain specialized cases require that the laser light is projected in the shape of the anatomy being treated (for example a long rectangle for treating the entire spine). Laser beam geometries and the limited capabilities of refractive lenses make it difficult to achieve ideal projections patterns or shapes. Lenses simply take the poor geometry of the laser beam and expand or compress it to a different size. Traditionally laser therapy devices use lenses to expand the laser beam, but have limited ability to alter the geometry. An operator compensates for these deficiencies by "painting" the treatment area. Some devices automatically steer the treatment head during use but these are very expensive. Finally, some devices use multiple laser diodes to provide simultaneous treatment over an area. What is needed is a laser therapy device that can disperse the output laser light in a wide variety of geometries in order to accommodate the requirement of different treatment modalities.

Laser therapy is characterized by dose-dependence, meaning that higher doses typically yield improved treatment outcomes. This has resulted in laser therapy devices becoming progressively more powerful over time. While higher power facilitates greater efficacy, it also increases the attendant risks of operating such devices. The high energy levels may cause injury if not properly administered. What is needed is a high-power laser therapy device that automatically regulates the energy output of the laser therapy device during treatment in order to reduce the risk of such injury.

The present invention is directed toward a cordless, high-powered, laser therapy device. Current high power therapy lasers are based upon surgical lasers, due to the maturity of surgical laser technology and the easy repurposing for therapy. However, surgical lasers were developed to be stationary since they were intended to be used on immobile patients. There was no need or desire to make a surgical laser as a handheld or cordless device. Patients are placed under general anesthetic and are brought to the machine's location.

Although surgical and therapy lasers are almost identical in construction, their uses are very different. These different uses give rise to opportunities for an improved design of a laser device for therapy, but also present significant engineering hurdles. Specifically;

(1) Surgical lasers are used to cut tissue to a defined depth. They have a very narrow range of uses. Therapeutic laser devices on the other hand are used for many different conditions including pain, inflammation, wound healing, neuromuscular reeducation and many others.

(2) When a surgical laser has sufficient power to perform an incision, additional power is neither beneficial nor desired. When used for therapy, higher power usually improves treatment (as long as tissue is not overheated). Thus there is a tendency to use higher power laser therapy devices as this improves both treatment outcomes and the time efficiency of treatment.

(3) Surgical lasers require a single narrow beam of light. Therapy lasers require a dispersed beam. A broad dispersed beam is often preferred for therapy because it enhances safety.

(4) Surgical lasers require exact control of power output as this determines the depth of cut. Therapy lasers are concerned more with "dose" or accumulated radiation, so lower power can be used at the expense of longer treatment time.

(5) Surgical lasers are required to heat tissue so hot that it evaporates, whereas therapy lasers must not be allowed to cause discomfort, let alone tissue damage.

(6) Surgical lasers are directed at a very small area with great precision. Therapy lasers are moved around to cover large areas resulting in higher probability of stray radiation.

Laser therapy devices vary principally in output power. The range is a few milliwatts to tens of watts. Like any light source, a laser diode is not 100% efficient. Waste energy is liberated as heat, so thermal management for high-power laser therapy devices is a major issue. Modern laser diodes are roughly 50% efficient. This means that half of the supplied electrical power is converted to light output and the other half is converted to heat. In high power laser therapy devices, this "waste" heat presents two engineering problems. Laser diode efficiency and life degrade at elevated temperatures. Dumping heat into the surrounding air requires a large cooling apparatus. Overheating is the most common cause of laser therapy device failures.

In addition, high power laser therapy devices consume significant electrical power. In order to operate as a cordless device, large batteries are required. This causes such devices to be overly heavy and cumbersome and be seen as impractical.

Therapy lasers have historically been repurposed surgical lasers. Manufacturers have simply applied different heads to diverge the beam (at the end of the fiber that carries the light output) and applied different software to existing surgical devices. Although some of these devices were "portable," they are portable only in the sense that the entire unit could be moved. There has yet to be a self-contained, handheld laser therapy unit. No manufacturer has yet designed and implemented such a therapy laser device. The most obvious reason is the ease of repurposing existing technology (surgical lasers). In addition, the creation of a portable, high-power, handheld laser therapy device requires a multidisciplinary approach to overcome engineering hurdles that span high-power optics, miniaturization of electronic, miniaturized of thermal imaging, advanced thermal management, energy management and ergonomics.

The present invention overcomes these limitations. One embodiment of the invention is directed toward a cordless, high-powered, laser therapy device. "High-powered" means any laser therapy device with optical power output of five (5) watts or higher, although the same technology could be employed to benefit lower power devices. The cordless, handheld, embodiment of the laser provides a great advantage in situations where a patient requires treatment in a specific position which would be awkward or impractical to treat with a corded device. Likewise, a cordless, handheld, laser therapy unit would be beneficial for treating animals in the care of a veterinarian.

Because of the limitations in the current state of the art, handheld laser therapy devices are not high powered. Laser diodes typically require around 20% of the maximum input electrical power before they start emitting light. Therefore at low output power levels the conversion rate of electrical power to optical power is very low.

The current invention uses a novel approach for improving efficiency of the laser diodes at lower output power requirements (and therefore minimizing electrical power consumption). The maximum efficiency of the laser diodes is when they are operating at maximum output power. The invention employs two mechanisms for adjusting the total output power of the device while the laser diodes are running at maximum output. Firstly, the invention disables a portion of the array of diodes. Those laser diodes that are switched on are operating at or near their maximum power but since there are fewer, the net laser power emitted from the device is reduced. The second mechanism is to pulse the diodes between off and on very rapidly and to vary the percentage of time that the diode is in the "on" state. This technique of "Pulse Width Modulation" is used to provide a much finer degree of control than selective disabling of parts of the laser diode array.

SUMMARY OF INVENTION

The invention is directed toward a handheld laser therapy device comprising one or more laser diodes, one or more microprocessor units, a user interface, and an external housing. The one or more microprocessor units contain nonvolatile memory storing a pulse-width-modulation algorithm to be executed by the one or more microprocessor units. The pulse-width-modulation algorithm comprises instructions which when executed by the one or more microprocessor units switches the electrical power to the one or more laser diodes on and off in a predetermined pattern. The one or more laser diodes, the one or more microprocessor units and the user interface are contained within the external housing. The one or more microprocessor units are coupled to the one or more laser diodes. The one or more laser diodes create one or more laser beams originating within the handheld unit and propagating from the handheld unit. The total laser output power of the device is equal to or greater than five watts.

In another embodiment of the invention the device further comprises an interchangeable power source. The interchangeable power source removably secures to the external housing.

In another embodiment of the invention the device further comprises a power source and a charging port. The power source and the charging port are contained within the external housing. The charging port is coupled with the power source.

In another embodiment of the invention the device further comprises an external power source and a power input port. The power input port is contained within the external housing. The external power source is electrically coupled with the power input port.

In another embodiment of the invention the device further comprises an interchangeable hood. The interchangeable hood comprises an identification chip and one or more optical elements. The one or more optical elements and the identification chip are contained within the interchangeable hood. The interchangeable hood removably secures to the external housing. The one or more laser beams pass through the one or more optical elements, the one or more optical elements propagating the one or more laser beams into a desired radiation pattern.

In another embodiment of the invention the identification chip is electrically connected to the handheld unit. The identification chip stores information regarding the function of the interchangeable hood. The one or more microprocessor units are configured to access the information in the identification chip and modify the activation of the one or more laser diodes depending on the information received from the identification chip. The modification is selected from a group consisting essentially of a variation in mean power output, a variation in time of energization, or a variation of wavelength of laser energy.

In another embodiment of the invention the device further comprises a temperature sensor. The temperature sensor is coupled to the one or more microprocessor units and is configured to continuously measure the temperature of the area being treated by the device. The one or more microprocessor units may use this temperature information to modify the activation of the one or more laser diodes to decrease the mean power output of the one or more laser diodes in order to prevent the treated area becoming excessively hot. The one or more microprocessor units may also deactivate the one or more laser diodes if the temperature measurements indicate that the device is not pointed at tissue. Furthermore, in other embodiments of the invention, the temperature sensor is a non-contact, far infrared sensor array. Furthermore, the thermal image may be analyzed by the one or more microprocessor units to identify areas that require treatment.

In other embodiments, the device may further comprise a thermoelectric heat pump, a heat sink, and a fan. The thermoelectric heat pump, the heat sink, and the fan are contained within the external housing. The one or more microprocessor units control the thermoelectric heat pump and fan in order to control the temperature of the one or more laser diodes. The thermoelectric heat pump transfers the waste heat produced by the one or more laser diodes to the heat sink, causing the temperature of the heat sink to increase. The fan forces air to pass over the heat sink, thus cooling the heat sink and expelling the warmed air outside of the device. The net effect of this design allows the one or more laser diodes to operate at a controlled temperature, thus improving electrical efficiency of the device and extending the operating life of the one or more laser diodes.

In another embodiment of the invention the device further comprises a wireless transceiver. The wireless transceiver is coupled to the one or more microprocessor units. The wireless transceiver is communicatively coupled to an external master controller. The master controller comprises a control means. The control means is configured to permit a user to control the operation of the handheld unit.

In another embodiment of the invention the device further comprises an analog control means. The analog control means regulates the amount of electrical power supplied to the laser diodes in order to control their optical output power.

In another embodiment of the invention the device further comprises an electronic display and an operator input means. The electronic display displays information pertaining to the operation of the laser therapy device. The operator input means permits a user to modify the operation of the laser therapy device. The electronic display and the operator input means are coupled with the one or more microprocessor units. The electronic display and the operator input means are contained within the external housing.

The invention is also directed toward a system for delivering a laser radiation pattern comprising the handheld unit, interchangeable hood, and a master controller. The master controller comprises a control means. The control means is configured to permit a user to control the operation of one or more handheld units.

The invention is also directed toward a method for treating a patient with a high-powered therapeutic laser therapy device. The method comprises holding a high-powered handheld laser therapy device, aim1ng the high-powered handheld laser therapy device such that the predetermined radiation pattern is projected onto a treatment area on a patient, and applying a predetermined amount of radiation to the treatment area to effect a therapeutic result.

The invention is also directed toward a method for adjusting a laser radiation pattern comprising removably securing a first interchangeable hood with a first identification chip to a handheld unit, activating one or more laser diodes in the handheld unit, and propagating the laser beams with one or more optical elements contained in the first interchangeable hood. The method may further comprise reading information from the first identification chip and modifying the activation of the one or more laser diodes via the one or more microprocessor units in the handheld unit based upon this information. The modification may be selected from a group consisting essentially of a variation in mean power output, a variation in time of energization, or a variation of wavelength of laser energy. The method may further comprise removing the first interchangeable hood from the handheld unit, removably securing a second interchangeable hood to the handheld unit, activating the laser diodes, and propagating the resulting one or more laser beams into a predetermined radiation pattern with the one or more second optical elements contained in the second interchangeable hood. The method may further comprise reading information from the second identification chip in the second interchangeable hood and modifying the activation of the one or more laser diodes via the one or more microprocessor units. In this method the one or more microprocessor units is configured to modify the activation of the one or more laser diodes based upon the information in the second identification chip.

BRIEF DESCRIPTION OF THE DRAWINGS

Various exemplary embodiments of this invention will be described in detail, wherein like reference numerals refer to identical or similar components, with reference to the following figures, wherein.

DETAILED DESCRIPTION OF THE PREFERRED EMBODIMENT

Figure 1A:
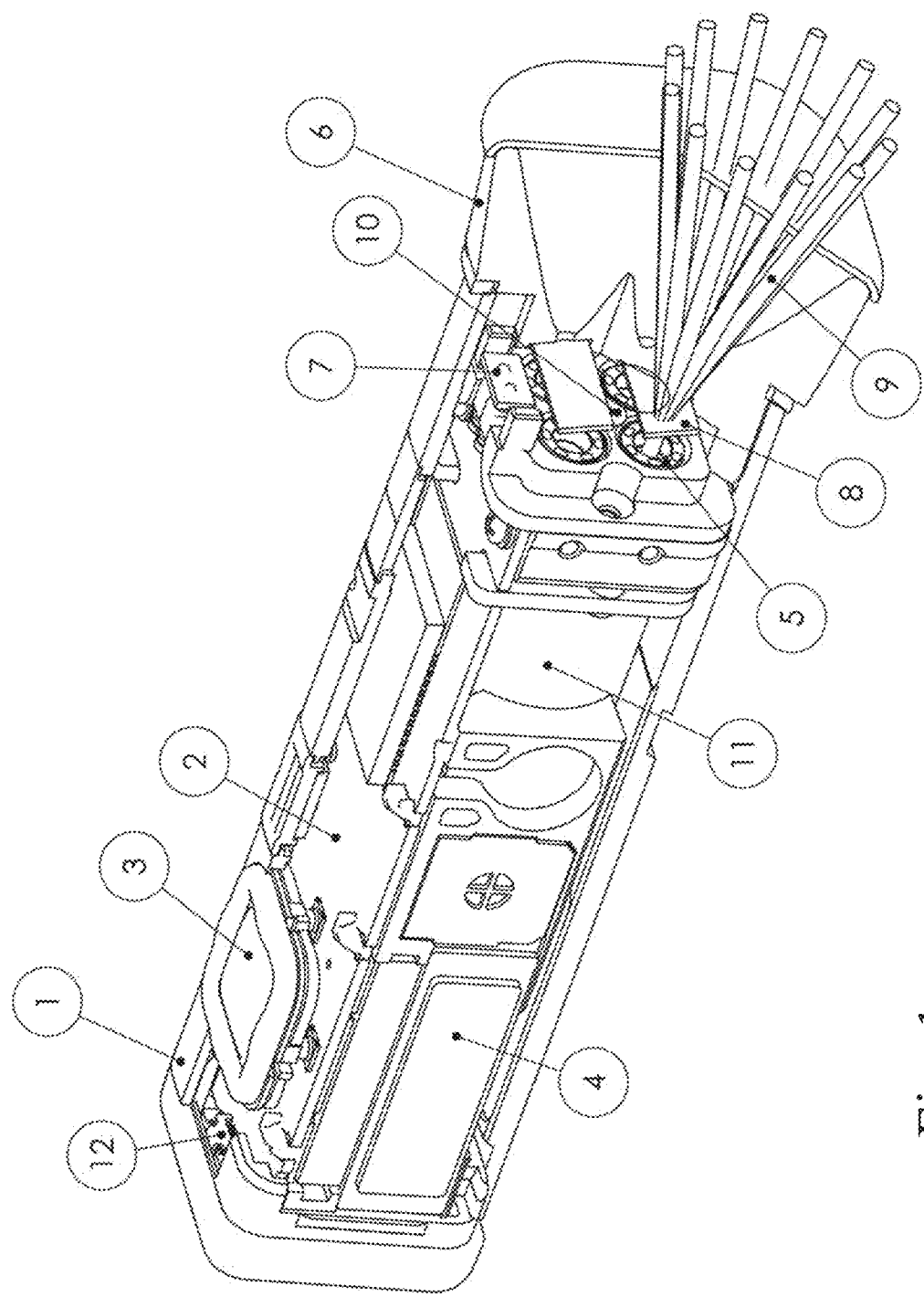
FIG. 1a is a perspective view of the laser therapy device.

The claimed subject matter is now described with reference to the drawings. In the following description, for purposes of explanation, numerous specific details are set forth in order to provide a thorough understanding of the claimed subject matter. It may be evident, however, that the claimed subject matter may be practiced with or without any combination of these specific details, without departing from the spirit and scope of this invention and the claims.

As used in this application, the terms "component", "module", "system", "interface", or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component.

The invention is directed toward a high power, handheld laser therapy device comprising one or more laser diodes, one or more microprocessor units, and an external housing. The one or more microprocessor units comprise a nonvolatile memory unit storing a pulse-width-modulation algorithm to be executed by the one or more microprocessor units. The pulse-width-modulation algorithm comprises instructions which when executed by the one or more microprocessor units switches the electrical power to the one or more laser diodes on and off in a predetermined pattern. The one or more laser diodes and the one or more microprocessor units are contained within the external housing. The one or more microprocessor units are coupled to the one or more laser diodes. The one or more laser diodes create one or more laser beams originating within the handheld unit and propagating from the handheld unit. The total laser output power of the device is equal to or greater than five watts.

Additionally, the invention is directed toward a laser therapy device which utilizes far-infrared measurement to determine the surface temperature of the patient's skin in order to reduce risk of injury. Far-infrared temperature sensing has become sufficiently small and inexpensive to integrate into the treatment head of laser therapy devices. This affords many benefits, including the identification of areas requiring treatment (inflamed tissue is hotter than surrounding tissue) and enhanced safety. To improve safety, a laser therapy device with thermal sensing can determine if it is pointed at human tissue (based on the temperature) and disable operation if it is not. By measuring the temperature of the area being treated, a laser therapy device with thermal sensing can automatically modulate the output power, and direct the operator to move the treatment head in order to ensure optimal, safe dosing. In the preferred embodiment, the invention uses a thermal imaging sensor to perform temperature measurement.

Laser diodes are the preferred source of laser radiation for therapy devices. Due to the wide range of conditions and treatment modalities, a necessary device feature is the control of output power. In some cases a low dose is required. However, laser didoes exhibit poor power efficiency at reduced output power. The invention uses a novel method for controlling the output power of each laser diode, using a combination of digital (Pulse Width Modulation) and analog techniques that allows efficient and stable control of laser diodes across a wide power range. In the preferred embodiment, the invention uses a plurality of laser diodes. In this preferred embodiment, the invention also controls the device output power by only activation some of the laser diodes.

In one embodiment of the invention the laser therapy device may further comprise a visual graphic user interface. Laser therapy devices benefit from graphic user interfaces for operator control. However, such handheld devices need to be as small and light as possible to reduce occupational burden and maximize utility. In order to resolve these competing requirements, one embodiment of the invention uses a wireless data connection to a master controller, which is a remote computing device such as a personal computer, tablet computer or smartphone in order to enhance the user's ability to control the device. The wireless connection allows full control of one or more devices, providing the means to configure and control the one or more devices using a software application with a much richer user interface than that of the device itself. This allows the device to be small and lightweight without compromising functionality.

The wireless data connection also allows devices to connect to one-another so that a community of devices may act in a synchronized manner. Handheld units can coordinate among each other via the wireless link, or be directed by the master controller to optimize treatment. For example, two handheld units can be placed on stands and focused on a particular area of the patient. A third handheld unit, operated by the practitioner can be used to control the operation of the other devices. This allows for coordinated treatment at different areas of the body. Precise synchronization of light signaling opens up new areas of treatment capability.

The visual graphic user interface may also utilize a help menu system which is dependent on the context of the use of the laser therapy device. Context-sensitive help is a mature design approach that is well used in computer software. This allows the user to request help for the current screen for specific information about that screen instead of scrolling through volumes of material. It is not uncommon to find such context-sensitive help systems on modern devices that are equipped with integrated displays. Advances in electronics now make it possible to include not only textual help, but also audio-visual tips, training and support on the actual device. The invention uses this capability to provide assistance for the treatment of specific conditions.

Referring to FIG. 1a, the handheld laser therapy device 1, or handheld unit, is displayed. The handheld laser therapy device 1 comprises a microprocessor unit 2, an operator input means 3, an electronic display 4, one or more laser sources (laser diodes) 5, a temperature sensor 10, and a power source (or battery) 11. Attached to handheld laser therapy device 1 is an interchangeable hood 6. The interchangeable hood 6 contains an identification chip 7 and one or more optical elements 8. The laser sources 5 create incident beams which pass through the diffractive optical elements 8 to create a radiation pattern 9. In addition, the handheld laser therapy device 1 may have a charging port 12 which recharges the power source 11.

Figure 1B:
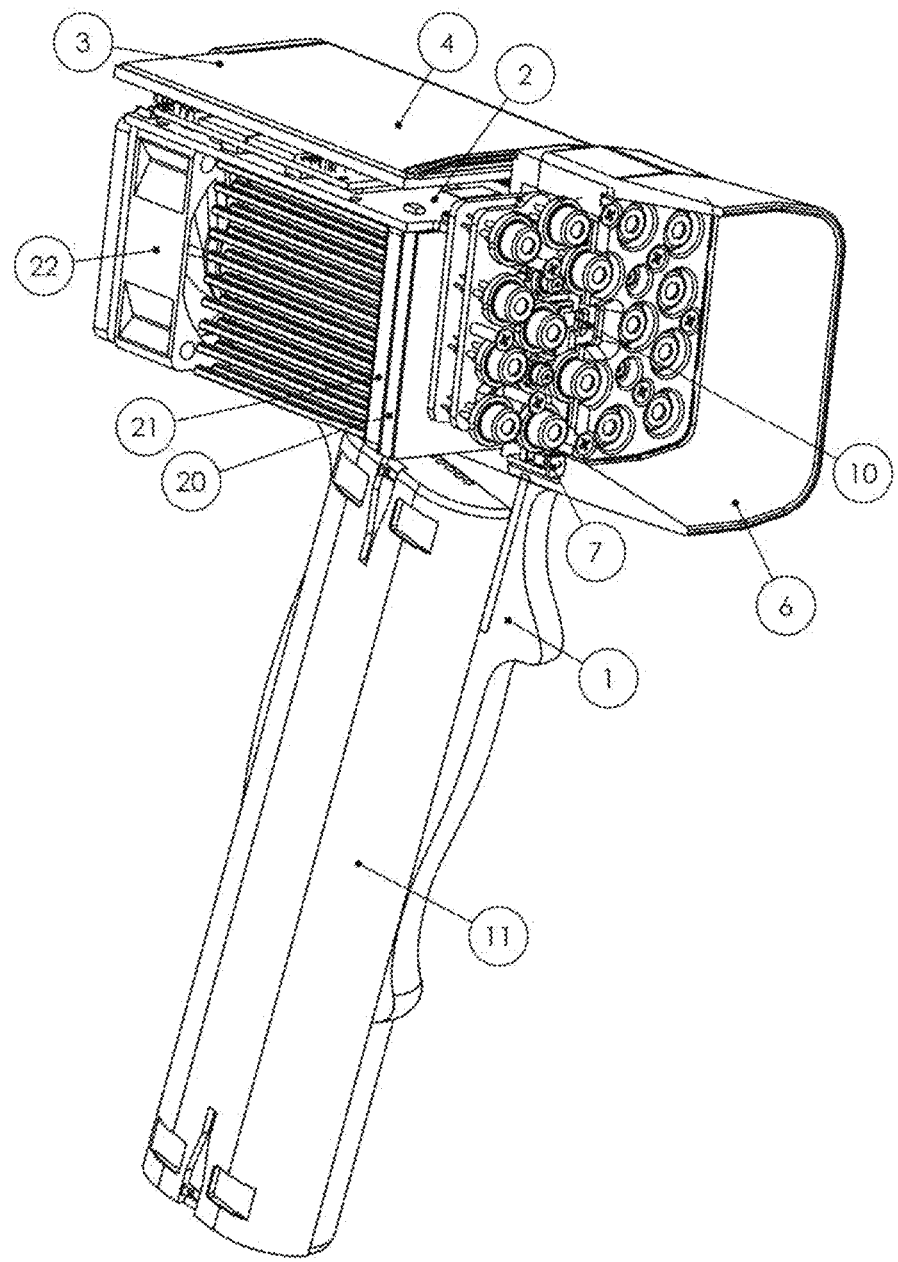
FIG. 1b is a perspective view of an alternative embodiment of the laser therapy device.

Referring to FIG. 1b, an alternative embodiment of the handheld laser therapy device 1 is displayed. In this embodiment of the invention, the handheld laser therapy device 1 comprises a microprocessor unit 2, an operator input means 3, an electronic display 4, one or more laser sources (laser diodes) 5, a temperature sensor 10, an interchangeable power source (or battery) 11, a thermo-electric cooler 20 (also known as a Peltier cooler), a heat sink 21, and a cooling fan 22. Attached to the handheld laser therapy device 1 is an interchangeable hood 6 utilizing an identification chip 7.

Figure 2:
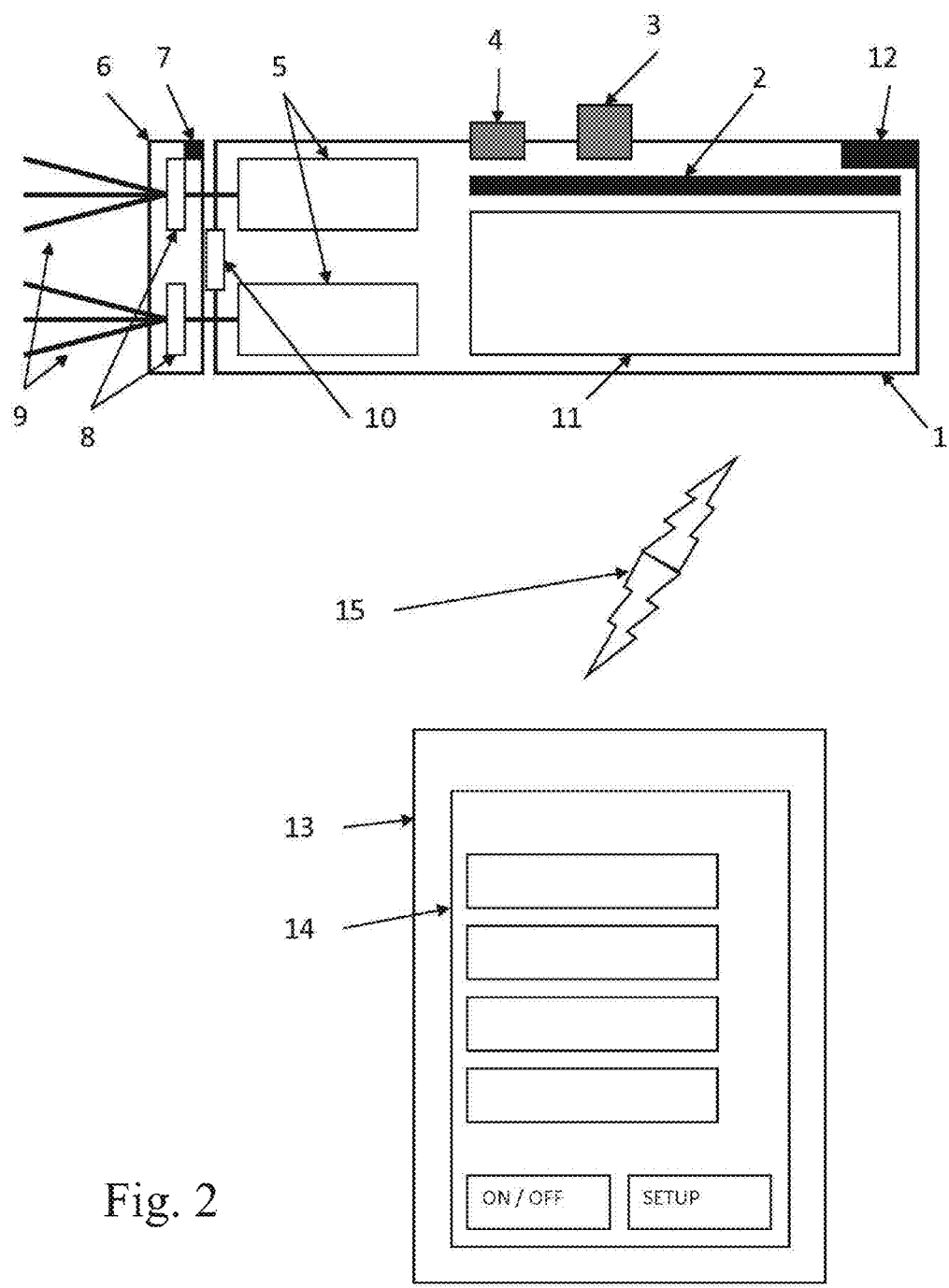
FIG. 2 is a schematic view thereof.

Referring to FIG. 2, a schematic displaying an optional utilization of the handheld therapy device 1 is displayed. As shown, the handheld laser therapy device 1 may be controlled by a master controller 13. The master controller 13 allows a user to control one or more handheld laser therapy devices 1. The remote controlling unit 13 may be any computing device, such as a cell phone, tablet, laptop computer, or computer, or a separate unit. The master controller 13 controls the handheld laser therapy device 1 by means of a wireless signal 15. In the preferred embodiment the master controller 13 utilizes a control means 14 to control the use of the handheld laser therapy device 1. The control means 14 may be a plurality of knobs and switches to control the variation of the output of the laser diodes 5. As displayed in FIG. 2, the control means 14 may be interactive software stored and executed on the master controller 13 that presents a visual user interface which permits the user to view information about the utilization of the handheld laser therapy device 1 and modify the utilization of the handheld laser therapy device 1.

The handheld laser therapy device 1 can be of any size and construction, but should preferably be of a minimize size and weight to improve usability and reduce occupational burden. In one embodiment, a device should ideally be no more than 5 inches in length, 1.5" in thickness, weighing no more than 8 ounces, although smaller and larger embodiments are anticipated as determined by the power capability of the device.

The microprocessor unit 2 is any type of microprocessor control unit or central processing unit. The microprocessor unit 2 may have read only access memory and/or random access memory utilized in the microprocessor unit 2 which would store and execute software instructions for the utilization of the handheld laser therapy device 1. The microprocessor unit 2 performs functions including, but not limited to, controlling the laser sources 5, reading and processing information from the temperature sensor 10, maintaining the wireless signal 15, managing charge in the power source 11, and managing the user interface (consisting of the operator input means 3, and the electronic display 4).

The microprocessor unit 2 has the capability to vary the output of the laser sources 5 in order to have the wide range of treatment capabilities. Absence of such controlling circuitry will result in a device that has fixed output power, limiting the device's utility. The microprocessor unit 2 can pulse the laser sources 5 at various frequencies and duty cycle. The microprocessor unit 2 can modulate the output of the laser sources 5 to create a time-varying output power. For example, the output power might be modulated to follow a sine wave at various frequencies, although other waveforms are contemplated. In addition, the microprocessor unit 2 can also selective disable one or more of the laser diodes 5.

Figure 3:
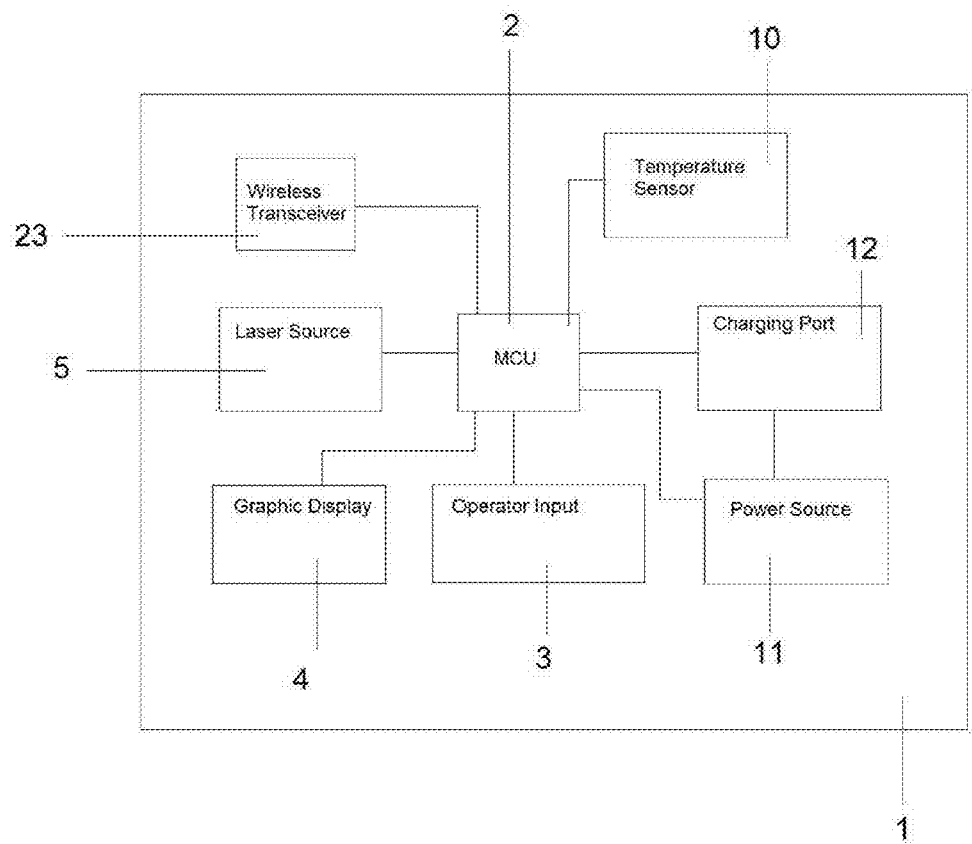
FIG. 3 is a schematic view thereof.

Referring to FIG. 3, a schematic displaying the interaction of the microprocessor unit 2 is displayed. In the preferred embodiment of the invention, the microprocessor unit 2 is connected to and controls all functionality of the handheld laser therapy device 1. In the preferred embodiment, the microprocessor unit 2 is connected to the operator input means 3, the electronic display 4, the laser sources 5, the temperature sensor 10, the power source 11, the charging port 12, and a wireless transceiver 23. The wireless transceiver 23 generates the wireless signal 15 allowing the handheld laser therapy device to communicate with the master controller 13.

The operator input means 3 is a control switch or touch screen that enables the operator to interact with the device. It should be understood that the operator input means 3 may be any type of component that is capable of allowing the user to operate the handheld laser therapy device 1, may be separate from or an integral part of the handheld laser therapy device 1, and that other embodiments of the operator input means 3 are anticipated.

The electronic display 4 provides information and feedback to the operator. This information includes but is not limited to: device settings, device status, thermal images, and treatment guides.

The laser sources 5 produce laser light under the control of the microprocessor unit 2. The handheld laser therapy device 1 may have any number of laser sources 5. In the preferred embodiment, the handheld laser therapy device 1 has multiple laser sources 5.

The interchangeable hood 6 is a replaceable component of various designs that are suited to specific treatment modalities. Variations of the optical elements 8 include elements that produce specific beam patterns, configurations of light pipes and optic fiber that combine, direct and focus radiation from one or more laser diodes 5. The optical elements 8 are components through which the laser beams traverse. The optical elements 8 may be diffractive optical elements which diffract the traversing laser beams to propagate the laser beams into a predetermined radiation pattern. Alternatively, the optical elements 8 may consist of light pipes, lenses, or optic fiber couplings. The interchangeable hood 6 may be in any shape or form which houses the optical elements 8. Other embodiments of the interchangeable hood 6 are anticipated.

The invention is directed toward a means for creating a predetermined therapeutic pattern from one or more laser beams with one or more diffractive optical elements. Specifically, the means comprises one or more laser diodes, generating one or more laser beams, and one or more diffractive optical elements configured to shape the one or more laser beams into a specific shape for therapeutic use. A diffractive optical element (DOE) is an optical device that can be designed to transform or shape an incident beam into almost any desired projected pattern. The projected pattern has a predetermined therapeutic function for use on a patient. The therapeutic function could be any health benefit provided to a patient-including humans and animals. The diffractive optical elements may be made of plastic or glass. The diffractive optical elements may be any size and shape.

Due to their light weight, small size and versatility, DOEs are well suited to the needs of laser therapy that requires specific radiation patterns. The invention uses DOEs as well as other lenses and light pipes to project the laser energy in an optimal manner for each of a range of treatment modalities.

The hood may also contain an identification chip 7 which contains information that uniquely identifies the hood. The microprocessor unit 2 reads and identifies the identification chip 7. In this manner the microprocessor unit 2 may configure the laser sources 5 according to the hood type.

The optical elements 8 convert an incident beam from the laser sources 5 into a pattern or shape, resulting in a specific radiation pattern 9. Many different patterns are anticipated, including but not limited to a circles, dots, shaded disks, and rectangles. To quickly and easily change from one radiation pattern 9 to another, a user simply changes the interchangeable hood 6 on the handheld laser therapy device 1.

Separate from the optical elements 8, the handheld laser therapy device 1 may have a temperature sensor 10. Thus the handheld laser therapy device 1 may have the temperature sensor 10 without having the optical elements 8 or the handheld laser therapy device 1 may have the optical elements 8 without having the temperature sensor 10.

The invention is also directed toward a means for measuring the temperature of an area subjected to an output of one or more laser diodes and adjusting the output of said one or more laser diodes based on said measurement. Specifically, this means comprises one or more temperature sensors 10 coupled to a microprocessor unit 2. The temperature sensor 10 measures the temperature of the surface area of the tissue being treated. This allows the device to regulate power within safe limits and also to provide alerts to the operator. The temperature sensor 10 may be any type of component capable of detecting the surface temperature of a patient's skin. The temperature sensor 10 may comprise a non-contact, far-infrared temperature sensor array such as a thermal imaging sensor which measures the temperature of the patient's skin without contact. Alternatively, the temperature sensor 10 may be a contact-based thermometer. The temperature sensor 10 measures the surface temperature of the patient's skin and sends the temperature information to the microprocessor unit 2. If the microprocessor unit 2 determines that the temperature of the tissue exceeds a preset level, then the microprocessor unit 2 cuts power to the laser sources 5 or otherwise modifies the activation of the laser sources 5 to set the treatment within safe parameters.

The invention is also directed toward a means for measuring the proximity of an area subjected to an output of one or more laser diodes and adjusting the output of said one or more laser diodes based on said measurement. Specifically, this means comprises one or more laser sources 5 and one or more temperature sensors 10 coupled to a microprocessor unit 2. The primary purpose of this means is to prevent the target tissue from becoming overheated. A secondary purpose is to use the temperature reading to detect the presence of living tissue. The temperature sensor 10 takes a reading of the temperature within the field of measurement of the temperature sensor 10. The reading taken by the temperature sensor 10 is sent to the microprocessor unit 2. The microprocessor unit 2 is configured to analyze the temperature reading to determine whether the treatment target of living tissue is proximal to, or distal from the handheld unit 100. The microprocessor unit 2 may also be configured to determine that the handheld unit 100 is not directed at living tissue and cease the operation of the laser sources 5. However, the measurement of temperature alone may not be sufficient to determine the proximity of the area subjected to the output of the laser sources 5. For instance, if clothing covers the treatment area the clothing can interfere with the temperature measurement. Therefore the means may include other embodiments, where the handheld unit 100 may further comprise a secondary proximity sensing unit to further permit a more reliable means of target detection.

The power source 11 powers the handheld laser therapy device 1. In the preferred embodiment, the power source 11 is a high capacity, rechargeable battery, but other embodiments are anticipated, including other technologies and physical implementations, such as a physically separate supply source that is electrically connected to the handheld laser therapy device 1. The charging port 12 is connected to the power source 11 and permits the power source 11 to be recharged through any means, such as by connecting the handheld laser therapy device 1 to a standard outlet.

The wireless link 15 is a WiFi radio link in the preferred embodiment, although other embodiments including Bluetooth and ZigBee are anticipated.

The master controller 13 is any computational device capable of controlling the use of the handheld laser therapy device 1. The master controller 13 is not a necessary part of the system and the handheld laser therapy device 1 may be utilized without the master controller 13. Depending on the physical size and shape of the master controller 13, it can be used to improve the operator's interaction with the handheld laser therapy device 1. In the preferred embodiment, the master controller 13 is a tablet computer or a smartphone. However, it should be recognized that other embodiments of the master controller 13 are anticipated, including other medical devices acting as the master controller 13.

The control means 14 may be controlling software. The controlling software can cooperate with multiple instances of the handheld laser therapy device 1 in order to synchronize operation of multiple instances of the handheld laser therapy device 1 in a precise manner. In one example, two handheld laser therapy devices 1 are configured to imitate the behavior of another handheld laser therapy device 1 which is designated as the master. The first two handheld laser therapy devices 1 thus act as slaves. Many other scenarios are anticipated, where multiple instances of handheld laser therapy devices 1 are coordinated to produce unique sequences.

In another scenario involving multiple instance of handheld laser therapy devices 1, one adopts the role of master controller, and the other devices are controlled exclusively by it. In this scenario, the handheld laser therapy device 1 informs the controlling software (over the wireless link 15) of its current operation and the controlling software then directs the other instances of the handheld laser therapy devices 1 to work in cooperation.

Figure 4:
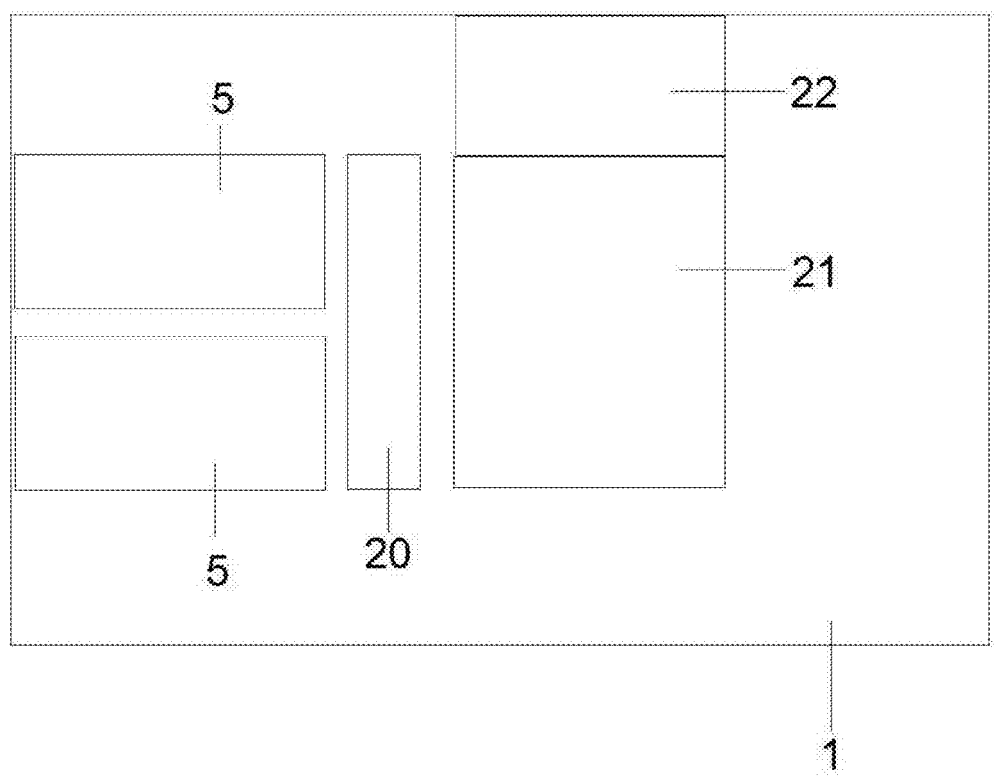
FIG. 4 is a schematic view of the heat management system of the laser therapy device.

Additionally, as displayed in FIG. 4, the handheld laser therapy device 1 utilizes a novel thermal management system to control the heat generated by the laser sources 5. The handheld laser therapy device's 1 configuration allows for passive and active thermal management. Part of the excess thermal heat generated is passively expelled. The handheld laser therapy device 1 also utilizes active monitoring of the heat generated by the laser. The handheld laser therapy device 1 utilizes a thermoelectric cooler 20 (such as a Peltier cooler) to cool the laser diodes 5. The generated heat by laser diodes 5 is transferred to a heat sink 21 to allow for further dissipation. The handheld laser therapy device 1 also utilizes a cooling fan 22 to increase air flow over heat sink 21 and through the unit to increase the cooling of the unit.

Additionally, the invention further comprises a means for automatically controlling the output power of the handheld laser therapy device 1. To meet the requirements of various treatment modalities, the handheld laser therapy device 1 must automatically control the power output by the laser diodes 5. The means for controlling the output power is the utilization of a pulsed duty cycle combined with analog control. In the preferred embodiment the means of automatically controlling the output power means is a set of executable instructions, which when executed by the microprocessor unit 2 control the output power and also pulse the modulation of the laser diodes 5. The microprocessor unit 2 may control the average output power produced by the laser diodes 5, by varying the power when the laser diodes are activated (analog control), and varying the percentage of time that the laser diodes are activated (pulse width modulation, digital control).

Figure 5:
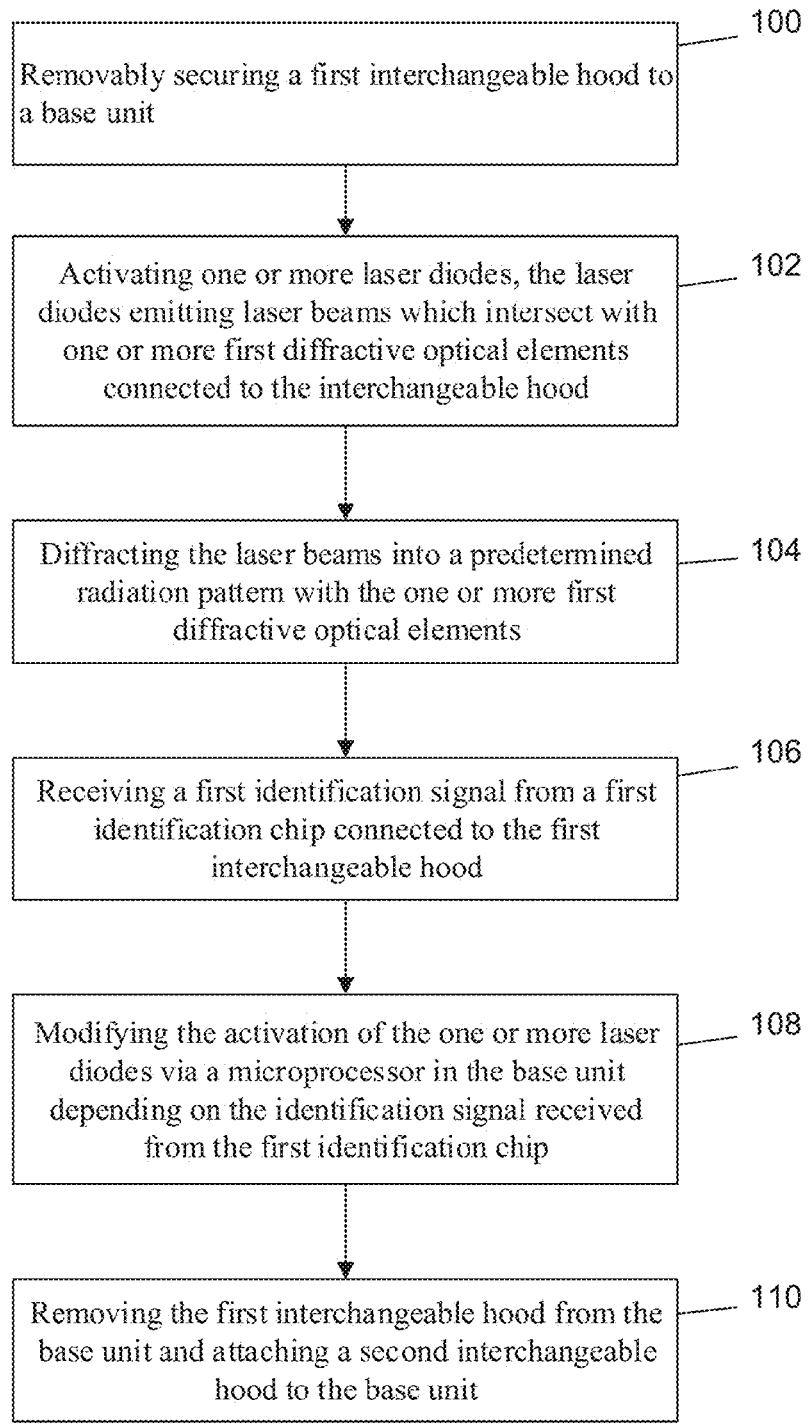
FIG. 5 is a view of the method of use of the invention.
Figure 6:
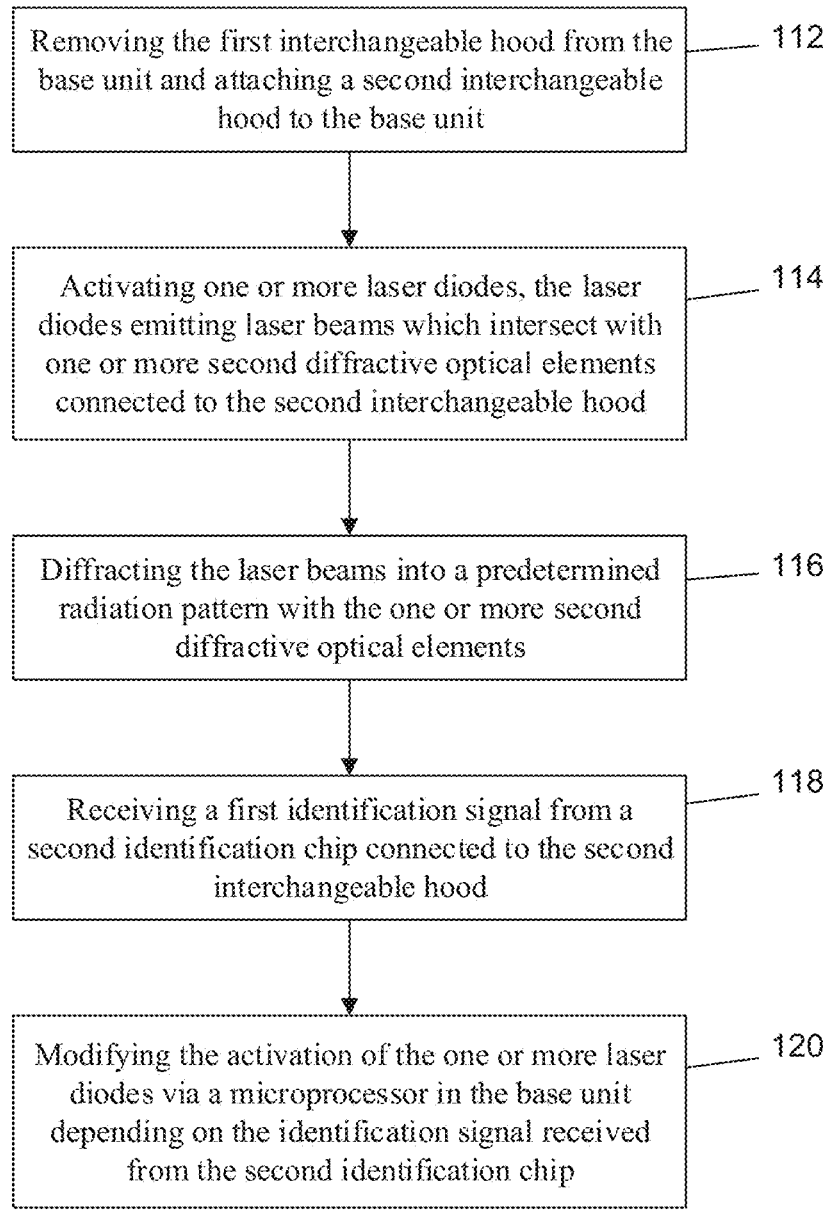
FIG. 6 is a view of the method of use of the invention.

Referring to FIG. 5 and FIG. 6 the method of utilizing the handheld laser therapy device 1 is displayed. First, a user removably secures a first interchangeable hood to the handheld unit 100. The user activates the laser diodes 102. The laser diodes generate laser beams which traverse with the optical elements housed in the interchangeable hood. The optical elements propagate the laser beams into a predetermined radiation pattern 104. The handheld unit receives a first identification signal from the first identification chip housed in the first interchangeable hood 106. The handheld unit modifies the activation of the laser diodes based upon the first identification signal received 108. When the user desires to change the radiation pattern the user removes the first interchangeable hood 110.

As shown in FIG. 6, the user can change the radiation pattern by removing the first interchangeable hood and attaching a second interchangeable hood 112. The user then activates the laser diodes 114. The optical elements of the second interchangeable hood propagate the laser beams into a predetermined radiation pattern that is different from the radiation pattern generated by the first interchangeable hood 116. The handheld unit receives a second identification signal from the second identification chip housed in the second interchangeable hood 118. The handheld unit then modifies the activation of the laser diodes based upon the second identification signal received 120.

Figure 7:
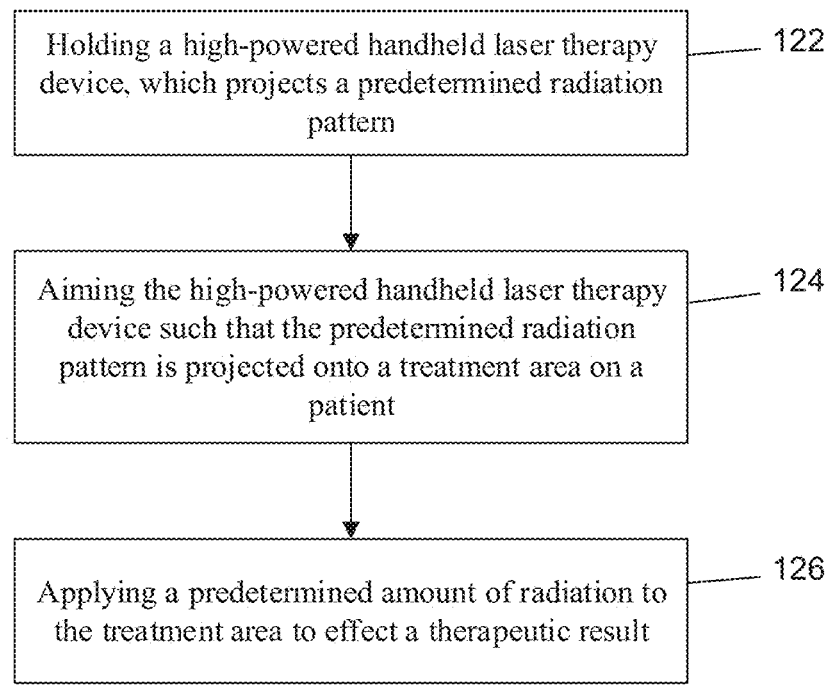
FIG. 7 is a view of the method of use of the invention.

Referring to FIG. 7, the method of utilizing the handheld laser therapy device 1 is displayed. A user starts by holding the high-powered handheld laser therapy device, which projects a predetermined radiation pattern 122. The user then aims the high-powered handheld laser therapy device such that the predetermined radiation pattern is projected onto a treatment area on a patient 124. The user then applies a predetermined amount of radiation to the treatment area to effect a therapeutic result 126.

What has been described above includes examples of the claimed subject matter. It is, of course, not possible to describe every conceivable combination of components or methodologies for purposes of describing the claimed subject matter, but one of ordinary skill in the art can recognize that many further combinations and permutations of such matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor unit, but, in the alternative, the processor may be any conventional processor, controller, microcontroller, or state machine. A processor may also be implemented as a combination of computing devices, e.g., a combination of a DSP and a microprocessor unit, a plurality of microprocessor units, one or more microprocessor units in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The steps of a method or algorithm disclosed herein may be embodied in a processor-executable software module, which may reside on a tangible, non-transitory computer-readable storage medium. Tangible, non-transitory computer-readable storage media may be any available media that may be accessed by a computer. By way of example, and not limitation, such non-transitory computer-readable media may comprise RAM, ROM, EEPROM, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable media. Additionally, the operations of a method or algorithm may reside as one or any combination or set of codes and/or instructions on a tangible, non-transitory machine readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

The invention claimed is:

1. A handheld laser therapy device comprising
   a. one or more laser diodes;
   b. one or more microprocessor units;
   c. an external housing;
   d. a user interface;
   e. a temperature sensor;
      i. wherein said temperature sensor is coupled to said one or more microprocessor units;
      ii. wherein said temperature sensor is configured to measure a temperature at one or more locations of an area subjected to said output of said one or more laser diodes;
      iii. wherein said temperature sensor is a non-contact, far infrared sensor array configured to generate a thermal image of a treatment area;
   f. wherein said one or more laser diodes and said one or more microprocessor units are contained within said external housing;
   g. wherein said one or more microprocessor units are coupled to said one or more laser diodes;
   h. wherein the output of said one or more laser diodes originates within said handheld device and propagates from said handheld device;
   i. wherein said one or more microprocessor units are configured to determine if said laser output is directed at human tissue based on thermal imaging readings from said temperature sensor;
   j. wherein said one or more microprocessor units are configured to disable all of said one or more laser diodes if said laser output is not directed at human tissue.

2. The device as in claim 1 further comprising an electronic display
   a. wherein said electronic display displays thermal images generated by said temperature sensor.

3. The device as in claim 2 wherein said one or more microprocessor units are configured to modulate the output power of said one or more laser diodes.

4. The device as in claim 3
   a. wherein said one or more microprocessor units are configured to determine when the surface temperature of the patient's skin exceeds a predetermined temperature;
   b. wherein said one or more microprocessor units are configured to lower the output power of one or more laser diodes when the surface temperature of the patient's skin exceeds said predetermined temperature.

5. A computerized method to be performed by a handheld laser therapy device
   a. wherein said handheld laser therapy device comprises
      i. one or more laser diodes;

ii. one or more microprocessor units;
iii. an external housing;
iv. a user interface;
v. a temperature sensor;
vi. wherein said temperature sensor is coupled to said one or more microprocessor units;
vii. wherein said temperature sensor is configured to measure a temperature at one or more locations of an area subjected to an output of said one or more laser diodes;
viii. wherein said temperature sensor is a non-contact, far infrared sensor array configured to generate a thermal image of a treatment area;
ix. wherein said one or more laser diodes and said one or more microprocessor units are contained within said external housing;
x. wherein said one or more microprocessor units are coupled to said one or more laser diodes;
xi. wherein the output of said one or more laser diodes originates within said handheld device and propagates from said handheld device;
b. wherein said method comprises
i. measuring, by said temperature sensor, a temperature of an area subjected to an output of said one or more laser diodes;
ii. transmitting a temperature reading from said temperature sensor to said one or more microprocessor units;
iii. comparing, by said one or more microprocessor units, said temperature reading to a predetermined temperature;
iv. altering, by said one or more microprocessor units, a laser output of said one or more laser diodes when said temperature reading exceeds said predetermined temperature.

6. The method as in claim 5 wherein the step of altering a laser output consists of ceasing all laser output of said one or more laser diodes.

7. The method as in claim 6 further comprising determining, by said one or more microprocessors, if said laser output is directed at human tissue based on thermal imaging readings from said temperature sensor.

8. The method as in claim 5 further comprising determining, by said one or more microprocessors, if said laser output is directed at human tissue based on thermal imaging readings from said temperature sensor.

9. The method as in claim 5 further comprising determining, by said one or more microprocessors, if said laser output is directed at human tissue based on thermal imaging readings from said temperature sensor.

10. A computerized method to be performed by a handheld laser therapy device
a. wherein said handheld laser therapy device comprises
i. one or more laser diodes;
ii. one or more microprocessor units;
iii. an external housing;
iv. a user interface;
v. a temperature sensor;
vi. wherein said temperature sensor is coupled to said one or more microprocessor units;
vii. wherein said temperature sensor is configured to measure a temperature at one or more locations of an area subjected to an output of said one or more laser diodes;
viii. wherein said temperature sensor is a non-contact, far infrared sensor array configured to generate a thermal image of a treatment area;
ix. wherein said one or more laser diodes and said one or more microprocessor units are contained within said external housing;
x. wherein said one or more microprocessor units are coupled to said one or more laser diodes;
xi. wherein the output of said one or more laser diodes originates within said handheld device and propagates from said handheld device;
b. wherein said method comprises
i. measuring, by said temperature sensor, a temperature of an area subjected to an output of said one or more laser diodes;
ii. transmitting a temperature reading from said temperature sensor to said one or more microprocessor units;
iii. comparing, by said one or more microprocessor units, said temperature reading to a predetermined temperature;
iv. generating, by said one or more microprocessors, a high temperature alarm when said temperature reading exceeds said predetermined temperature.

11. The method as in claim 10 further comprising determining, by said one or more microprocessors, if said laser output is directed at human tissue based on thermal imaging readings from said temperature sensor.

* * * * *